(12) United States Patent
Lehn et al.

(10) Patent No.: US 6,316,422 B1
(45) Date of Patent: ***Nov. 13, 2001

(54) COMPOUNDS RELATED TO THE AMIDINIUM FAMILY, PHARMACEUTICAL COMPOSITIONS CONTAINING SAME, AND USES THEREOF

(75) Inventors: Jean-Marie Lehn, Strasbourg; Pierre Lehn, Paris; Jean-Pierre Vigneron, Boissy-sur-Saint-Yon, all of (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/706,619

(22) Filed: Nov. 6, 2000

Related U.S. Application Data

(6362) Continuation of application No. 09/125,825, filed as application No.PCT/FR97/00364 on Feb. 28, 1997, now Pat. No. 6,143,729.

(30) Foreign Application Priority Data

Mar. 1, 1996 (FR) .................................................. 96 02604
Jul. 30, 1996 (FR) .................................................. 96 09557

(51) Int. Cl.[7] .......................... A01N 43/04; A61K 31/70; A61K 9/127; C07C 69/74; C12N 5/00
(52) U.S. Cl. ......................... 514/44; 424/450; 264/4.1; 264/4.3; 554/1; 560/1; 435/6; 435/325
(58) Field of Search ............................... 536/23.1; 435/6, 435/325; 424/450, 417, 1.21, 1.45, 9.321; 514/44; 554/1; 560/1; 264/4.1, 4.3

(56) References Cited

U.S. PATENT DOCUMENTS 5,811,406 * 9/1998 Szoka, Jr. et al. ..................... 514/44

* cited by examiner

Primary Examiner—John L. LeGuyader
Assistant Examiner—Janet L. Epps
(74) Attorney, Agent, or Firm—Synnestvedt & Lechner LLP

(57) ABSTRACT

Novel amidinium derivatives of formula (I), wherein R1 is a cholesterol derivative or an alkylamino-NR'R" grouping, and each of R2 and R3 is independently a hydrogen atom or a grouping of formula (II), wherein each of R4 and R5 is independently a hydrogen atom or a grouping of formula (III), are disclosed. The corresponding pharmaceutical compositions, which are particularly useful in gene therapy for transferring therapeutic genes into cells, are also disclosed.

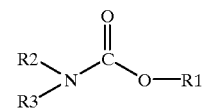

I

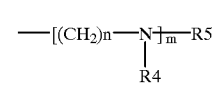

II

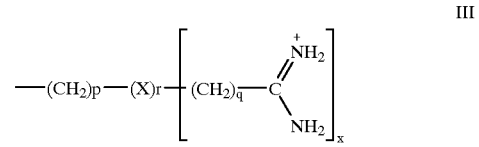

III

14 Claims, 8 Drawing Sheets

Figure 1:
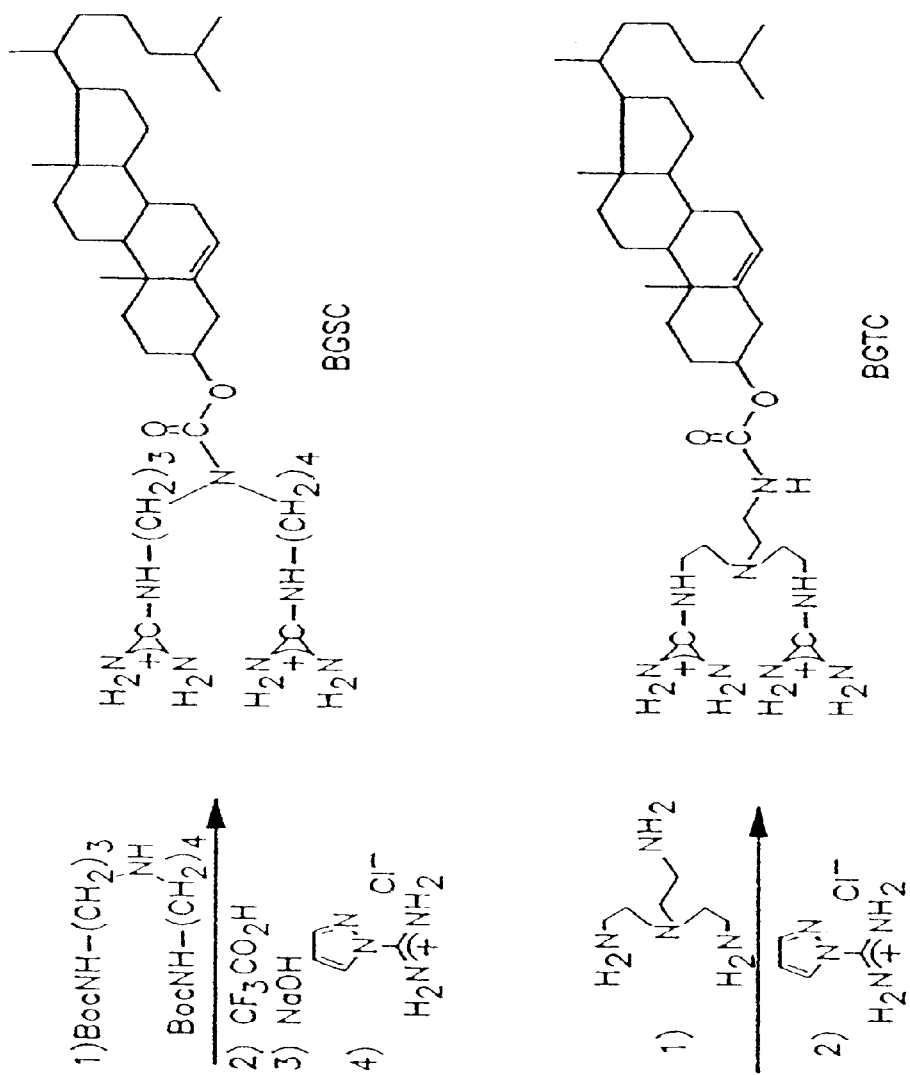
Figure 1:
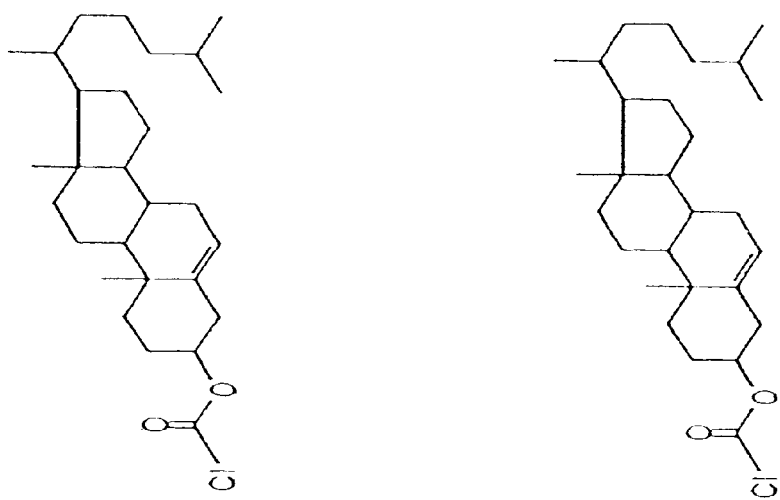

COMPOUNDS RELATED TO THE AMIDINIUM FAMILY, PHARMACEUTICAL COMPOSITIONS CONTAINING SAME, AND USES THEREOF

This is a continuation of application Ser. No. 09/125,825, filed Sept. 11, 1998, now U.S. Pat. No. 6,143,729, which is a a 371 of PCT/FR97/00364, filed Feb. 28, 1997, which claims priority to French Application No. FR 96/02,604, filed Mar. 1, 1996, and to French Application No. FR 96/09,557, filed Jul. 30, 1996.

The present invention relates to new compounds related to the amidinium family, including in particular the guanidiniums, pharmaceutical compositions containing them and their applications.

More precisely, the present invention relates to compounds of general formula I and their salts

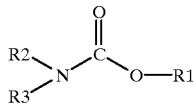

in which:
R1 represents a cholesterol derivative or an alkylamino —NR'R" group with R' and R" representing, independently of each other, a saturated or unsaturated, linear or branched $C_{12}$ to $C_{22}$ aliphatic radical.
R2 and R3 represent, independently of each other, a hydrogen atom or a group of general formula II with at least one of them being different from a hydrogen atom.

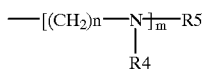

in which;
n and m represent, independently of each other and distinctly between the groups R2 and R3, an integer between 0 and 4,
R4 and R5 represent, independently of each other, a hydrogen atom or a group of formula III:

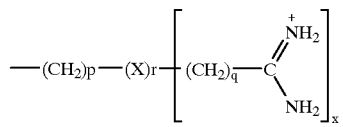

in which
p and q represent, independently of each other, an integer between 0 and 4 and r is equal to 0 or 1, with the condition that when r is equal to 1
X represents an NH group and x is equal to 1 or
X represents a nitrogen atom and x is equal to 2 and
it being possible for p, q and r to vary independently between the groups R4 to R5.
By way of preferred subfamily, there may be mentioned more particularly within the framework of the present invention the compounds of general formula I in which R2 or R3 represent, independently of each other, a hydrogen atom or a group of formula IV:

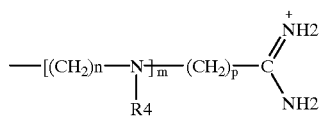

in which
n, m and p are as defined above and R4 represents a hydrogen atom or a group of formula V:

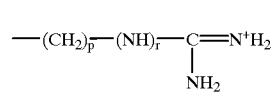

with q and r as defined above,
and it being possible for m, n, p, q and r to vary independently between the different groups R2 and R3.

These new products of general formula (I) may be provided in the form of nontoxic and pharmaceutically acceptable salts. These nontoxic salts comprise the salts with inorganic acids (hydrochloric, sulphuric, hydrobromic, phosphoric or nitric acids) or with organic acids (acetic, propionic, succinic, maleic, hydroxymaleic, benzoic, fumaric, methane-sulphonic or oxalic acids) or with inorganic bases (sodium hydroxide, potassium hydroxide, lithium hydroxide or calcium hydroxide) or organic bases (tertiary amines such as triethylamine, piperidine or benzylamine).

As representatives of the compounds according to the invention, there may be mentioned more particularly the compounds of the following general subformulae:

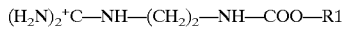
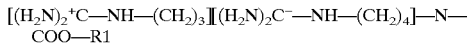
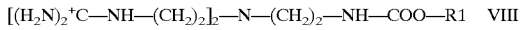
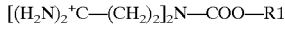
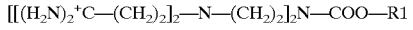

in which R1 has the above meaning.

As representatives of the claimed guanidiniums and amidiniums, there may be mentioned more particularly the compounds of the above subformulae VII, VIII and IX with R1 representing therein a cholesteryl group. The three compounds will be respectively identified hereinafter by the name BGSC (Bis Guanidino Spermidine Cholesterol) and BGTC (Bis Guanidino Tren Cholesterol) and BADC (Bis Amidinium Diethylenetriamine Cholesterol bishydrochloride).

The claimed compounds are most particularly advantageous from the therapeutic point of view for their nontoxic characteristics and their amphiphilic properties. Given these qualities, they may in particular be used for complexing nucleic acids in the perspective of cellular transfection thereof. These compounds may therefore be advantageously used in gene therapy.

Compounds VII (BGSC) and VIII (BGTC) are most particularly advantageous for in vivo gene transfer. These two compounds form a complex with DNA and protect it against degradation due to pH variations during transport to the cell to be treated.

The invention therefore relates to a pharmaceutical composition which comprises at least one compound according to the invention. In a preferred embodiment of the invention, the compound is Bis Guanidino Spermidine Cholesterol (BGSC) and in another preferred embodiment, the compound is Bis Guanidino Tren Cholesterol (BGTC).

The principal objective of gene therapy is to correct genetic diseases associated with a defect in expression and/or an abnormal, that is to say a deficient or excessive, expression of one or more nucleic acids. Efforts are being made to correct this type of genetic abnormality through cellular expression in vivo or in vitro of cloned genes.

Nowadays, several methods are proposed for the intracellular delivery of this type of genetic information. One of the technologies currently used is based precisely on the use of chemical or biochemical vectors. These synthetic vectors have two principal functions: compacting the DNA to be transfected and promoting its cellular attachment as well as its passage across the plasma membrane and, where appropriate, across the two nuclear membranes. Positively charged cationic lipids such as N-[1-(2,3-dioleyloxy) propryl]-N,N,N-trimethylammonium chloride (DOTMA) have thus been proposed. Advantageously, they interact, in the form of liposomes or of small vesicles, spontaneously with DNA, which is for its part negatively charged, to form lipid-DNA complexes capable of fusing with the cell membranes, and thus allowing the intracellular delivery of the DNA. However, in the specific case of DOTMA, its good efficiency in transfection unfortunately remains associated with a defect in biodegradability and a toxic character towards cells.

Since DOTMA, other cationic lipids have been developed on this model of structure: lipophilic group combined with an amino group via a so-called "spacer" arm. Among these, there may be mentioned more particularly those comprising, as lipophilic group, two fatty acids or a cholesterol derivative, and comprising, in addition, where appropriate, as amino group, a quaternary ammonium group. DOTAP, DOET or ChOTB may be mentioned in particular as representatives of this category of cationic lipids.

By virtue of their chemical structure and their biodegradable character, the claimed compounds meet precisely the requirements needed for a nucleic acid transfection vector.

The present invention therefore also relates to any application of these new compounds in the in vitro, ex vivo and/or in vivo transfection of cells and in particular for the vectorization of nucleic acids. It relates in particular to any pharmaceutical composition comprising a nucleic acid in addition to at least one compound according to the invention.

In the compositions of the present invention, the nucleic acid combined with at least one claimed compound may be either a deoxyribonucleic acid or a ribonucleic acid. These may be oligonucleotide or polynucleotide sequences of natural or artificial origin, and in particular genomic DNA, cDNA, mRNA, tRNA, rRNA, hybrid sequences or synthetic or semisynthetic sequences. These nucleic acids may be of human, animal, plant, bacterial or viral origin and the like. They preferably comprise a therapeutic gene.

Another object of the invention therefore relates to a pharmaceutical composition containing, in addition, a nucleic acid. Preferably, this nucleic acid is either a deoxyribonucleic acid or a ribonucleic acid. In a preferred embodiment of the invention, the nucleic acid comprises a therapeutic gene.

For the purposes of the invention, therapeutic gene is understood to mean in particular any gene encoding a protein product having a therapeutic effect. The protein product thus encoded may be a protein, a peptide or the like.

This protein product may be homologous with respect to the target cell (that is to say a product which is normally expressed in the target cell when the latter exhibits no pathology). In this case, the expression of a protein makes it possible, for example, to compensate for an insufficient expression in the cell or for the expression of a protein which is inactive or weakly active because of a modification, or alternatively to overexpress the said protein. The therapeutic gene may also encode a mutant of a cellular protein having increased stability, a modified activity and the like. The protein product may also be heterologous with respect to the target cell. In this case, an expressed protein may, for example, supplement or provide an activity which is deficient in the cell, allowing it to combat a pathology, or stimulate an immune response.

Among the therapeutic products for the purposes of the present invention, there may be mentioned more particularly enzymes, blood derivatives, hormones, lymphokines: interleukins, interferons, TNF and the like (FR 92/03120), growth factors, neuro-transmitters or precursors thereof or synthesis enzymes, trophic factors: BDNF, CNTF, NGF, IGF, GMF, aFGF, bFGF, NT3, NT5, HARP/pleiotrophin and the like, dystrophin or a minidystrophin (FR 91/11947), the protein CFTR associated with cystic fibrosis, tumour suppressor genes: p53, Rb, Rap1A, DCC, k-rev and the like (FR 93/04745), the genes encoding factors involved in clotting: factors VII, VIII and IX, the genes involved in DNA repair, suicide genes (thymidine kinase, cytosine deaminase), genes for haemoglobin or other carrier proteins, genes corresponding to the proteins involved in the metabolism of lipids, of the apolipoprotein type chosen from apolipoproteins A-I, A-II, A-IV, B, C-I, C-II, C-III, D, E, F, G, H, J and apo(a), metabolic enzymes such as for example lipoprotein lipase, hepatic lipase, lecithin cholesterol acyltransferase, 7-alpha-cholesterol hydroxylase, phosphatidic acid phosphatase, or alternatively proteins for transfer of lipids such as the protein for transfer of cholesterol esters and the protein for transfer of phospholipids, a protein for binding HDLs or alternatively a receptor chosen, for example, from the LDL receptors, receptors for remnant chylomicrons and scavenger receptors, and the like.

The therapeutic nucleic acid may also be a gene or a antisense sequence, whose expression in the target cell makes it possible to control the expression of genes or the transcription of cellular mRNAs. Such sequences may, for example, be transcribed in the target cell into RNAs complementary to cellular mRNAs and thereby block their translation into protein, according to the technique described in Patent EP 140 308. The therapeutic genes also comprise the sequences encoding ribozymes, which are capable of selectively destroying target RNAs (EP 321 201).

As indicated above, the nucleic acid may also comprise one or more genes encoding an antigenic peptide capable of generating an immunoresponse in man or in animals. In this specific embodiment, the invention therefore allows the production either of vaccines or of immunotherapeutic treatments applied to man or to animals, in particular against microorganisms, viruses or cancers. This may represent in particular antigenic peptides specific for the Epstein-Barr virus, the HIV virus, the hepatitis B virus (EP 185 573), the pseudorabies virus, the syncitia forming virus or other viruses, or alternatively specific for tumours (EP 259 212).

Preferably, the nucleic acid also comprises sequences allowing the expression of the therapeutic gene and/or of the gene encoding the antigenic peptide in the cell or desired organ. They may be sequences which are naturally responsible for the expression of the gene considered when these sequences are capable of functioning in the infected cell. They may also be sequences of different origin (responsible for the expression of other proteins, or even synthetic). In particular, they may be promoter sequences of eukaryotic or viral genes. For example, they may be promoter sequences derived from the genome of the cell which it is desired to infect. Likewise, they may be promoter sequences derived from the genome of a virus. In this regard, there may be mentioned, for example, the promoters of the E1A, MLP, CMV and RSV genes and the like. In addition, these expression sequences can be modified by the addition of activating or regulatory sequences and the like. The promoter may be inducible or repressible.

Moreover, the nucleic acid may also comprise, in particular upstream of the therapeutic gene, a signal sequence directing the therapeutic product synthesized in the secretory pathways of the target cell. This signal sequence may be the natural signal sequence of the therapeutic product, but it may also be any other functional signal sequence, or an artificial signal sequence. The nucleic acid may also comprise a signal sequence directing the therapeutic product synthesized to a specific compartment of the cell.

The cationic lipids described in the present invention, and in particular BGTC and BGSC, are capable of forming a complex with DNA, and represent an advantageous alternative to viral vectors for the transfer of nucleic acids of therapeutic interest, in vitro, ex vivo or in vivo. Because of the chemical properties of the guanidinium groups, and in particular their high pKa, these cationic lipids are capable of protecting DNA molecules against degradations due to pH variations. The results presented in the example show that these compounds allow the transfection of numerous cell types with a high efficiency. The transfection efficiency depends, in particular, on the cationic lipid/DNA ratio in the complexes formed. A ratio between the two compounds which is particularly favourable for transfection consists in having 6 to 8 guanidinium groups for one phosphate group on the DNA.

The transfection efficiency of the cationic lipid/DNA complexes may, in addition, be improved by addition of neutral lipid and formation of cationic liposomes. These liposomes are formed by a complex between the cationic lipid and the neutral lipid. The latter may be chosen from:

dioleoylphosphatidylethanolamine (DOPE), oleoylpalmitoylphosphatidylethanolamine (POPE), di-stearoyl, -palmitoyl, -mirystoyl phosphatidylethanolamine their derivatives which are N-methylated 1 to 3 times;

phosphatidylglycerols, diacylglycerols, glycosyldiacylglycerols, cerebrosides (such as in particular galactocerebrosides), sphingolipids (such as in particular sphingomyelins)

and asialogangliosides (such as in particular asialoGM1 and GM2).

Preferably DOPE is used.

Preferably, the compound of the invention, and the neutral lipid are present in a ratio of between 1 and 5, more preferably 2 and 4. In addition, the total lipid (compound of the invention plus neutral lipid) to DNA ratio is advantageously chosen such that the net ratio of positive charges is between 2 and 5. Particularly advantageously, the ratio is about 3.

The invention therefore also relates to any pharmaceutical composition comprising a compound according to the invention, a neutral lipid and a nucleic acid. Preferably, the compound according to the invention is chosen from BGTC and BGSC. Equally preferably, the neutral lipid is DOPE. The nucleic acid is either a deoxyribonucleic acid or a ribonucleic acid. Preferably, the nucleic acid comprises a therapeutic gene.

In addition to this application of the claimed amidinium derivatives, it is also possible to envisage enhancing their value in the following applications: interference in interactions between nucleic acids and proteins resulting in an inhibition or stimulation of certain processes, for example, for regulating genetic expression or enzymatic activity (polymerase, transcriptase and the like), selective complexing of anionic species for their extraction, their removal or their detection with the aid of membrane electrodes/probes for example, use as laboratory reagent for carrying out in vitro transfection operations, and the like.

Consequently, the subject of the present invention is also any therapeutic application of the amindinium derivatives as described above, either directly or in pharmaceutical compositions.

Preferably, the pharmaceutical compositions of the invention also contain a pharmaceutically acceptable vehicle for an injectable formulation, in particular for a direct injection at the level of the desired organ, or for administration by the topical route (on the skin and/or mucous membrane). They may be in particular isotonic, sterile solutions or dry, in particular freeze-dried, compositions which, upon addition, depending on the case, of sterilized water or of physiological saline, allow the constitution of injectable solutions.

The present invention will be more fully described with the aid of the following examples and figures which should be considered as illustrative and nonlimiting.

FIGURES

FIG. 1: Schematic representation of the operating protocols for preparing BGSC and BGTC.

Figure 2:
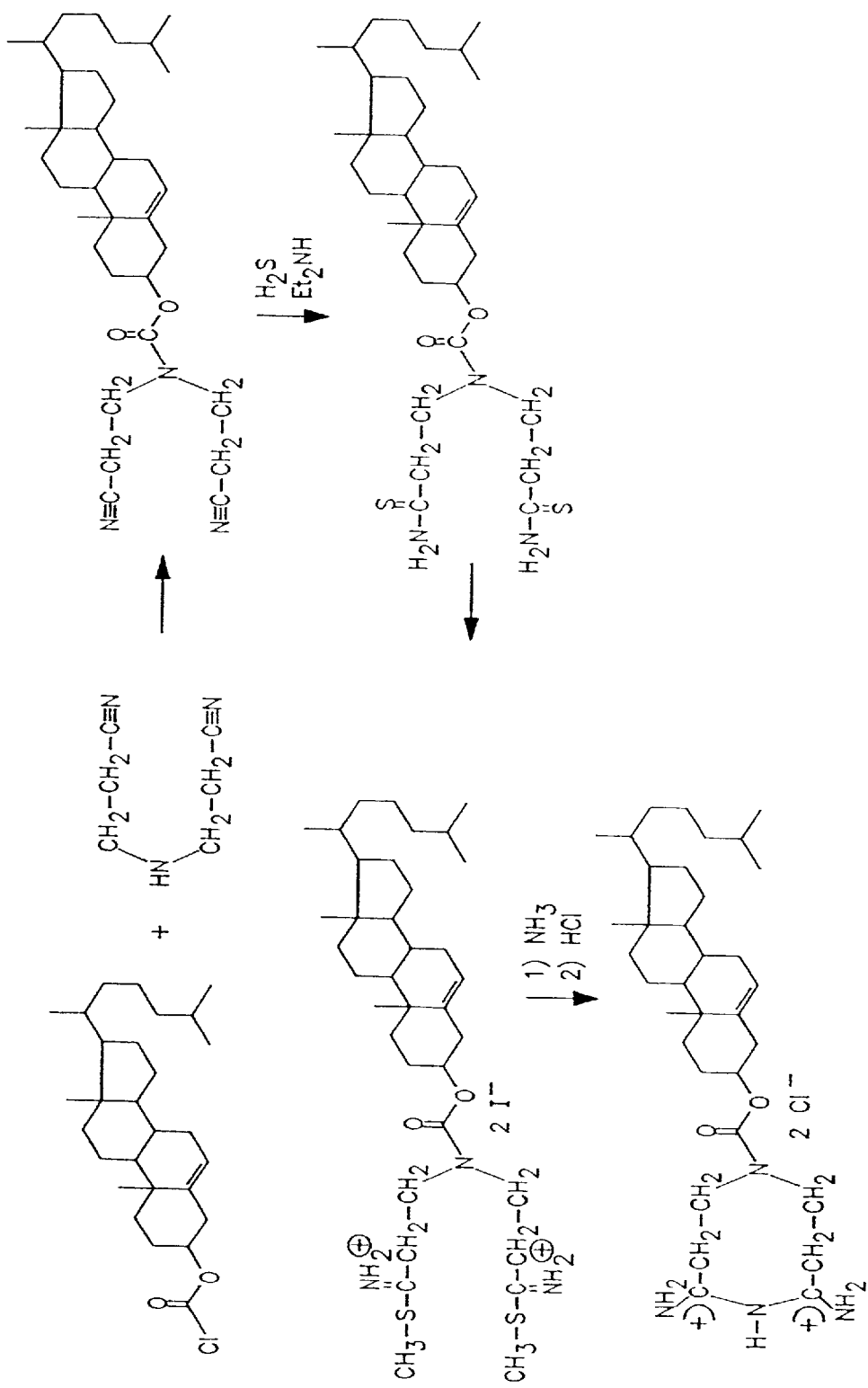

FIG. 2: Schematic representation of the operating protocols for preparing BADC.

Figure 3:
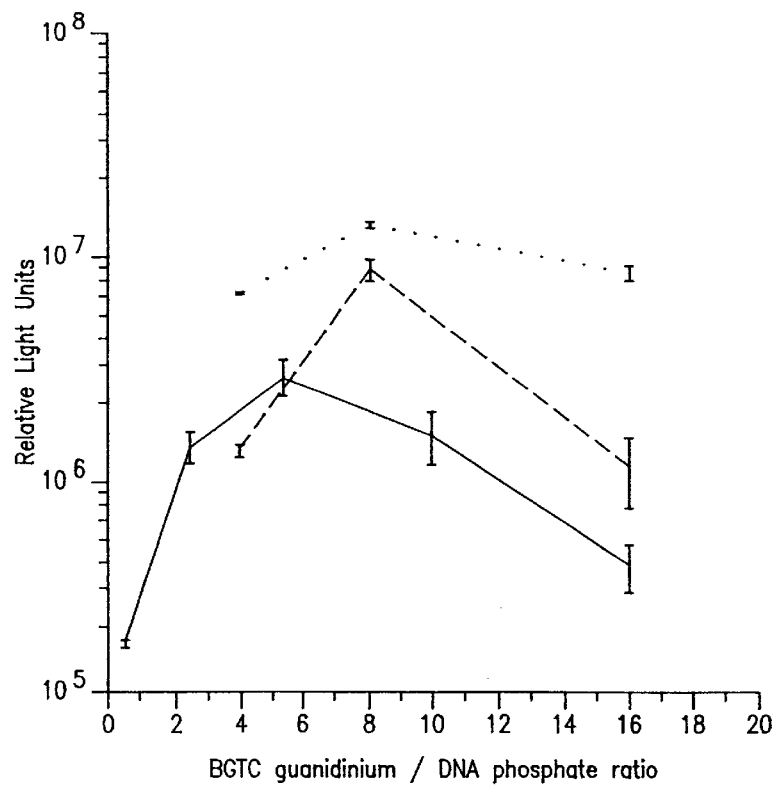

FIG. 3: Measurement of the transfection efficiency as a function of the lipid compound/DNA ratio.

Figure 4:
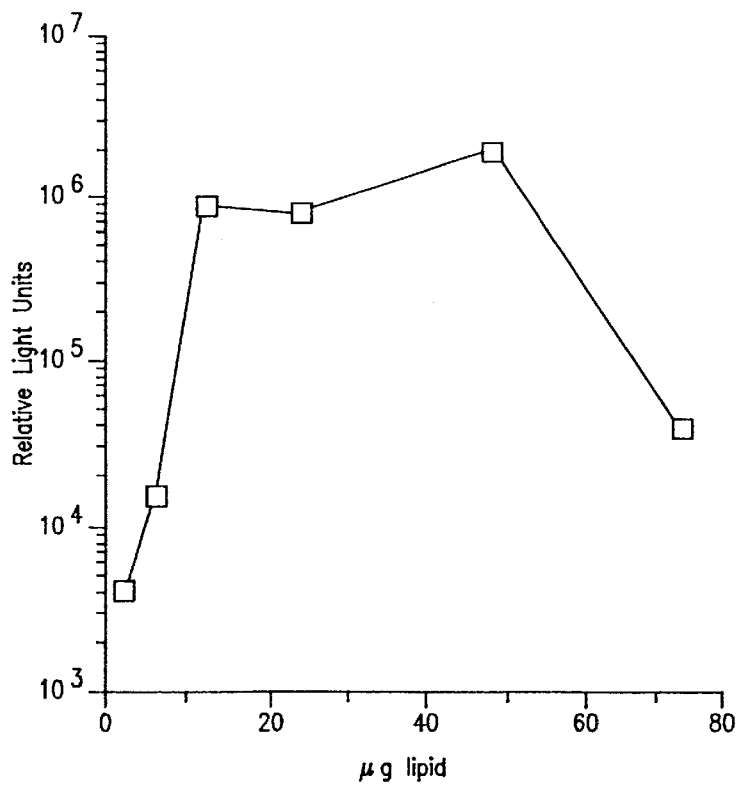
Figure 5A:
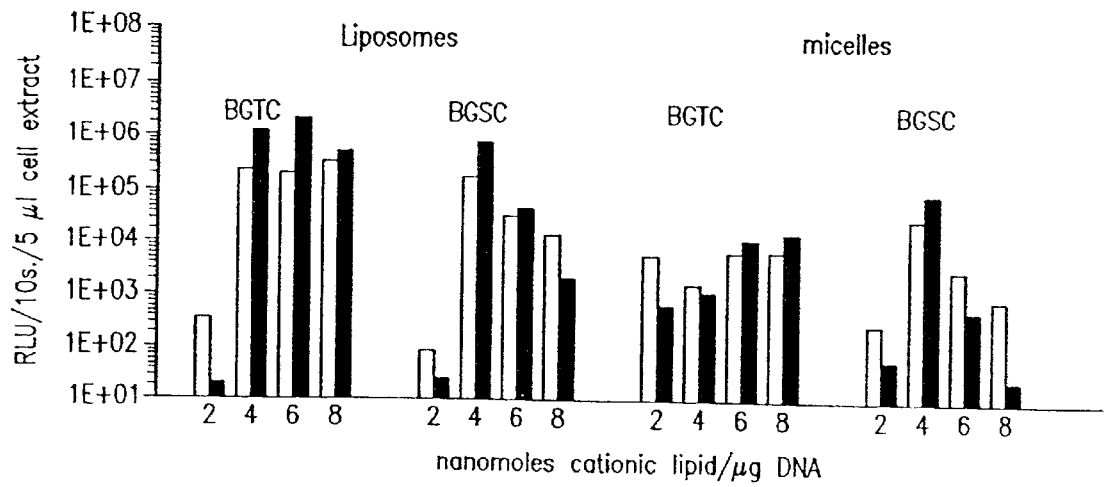
Figure 5B:
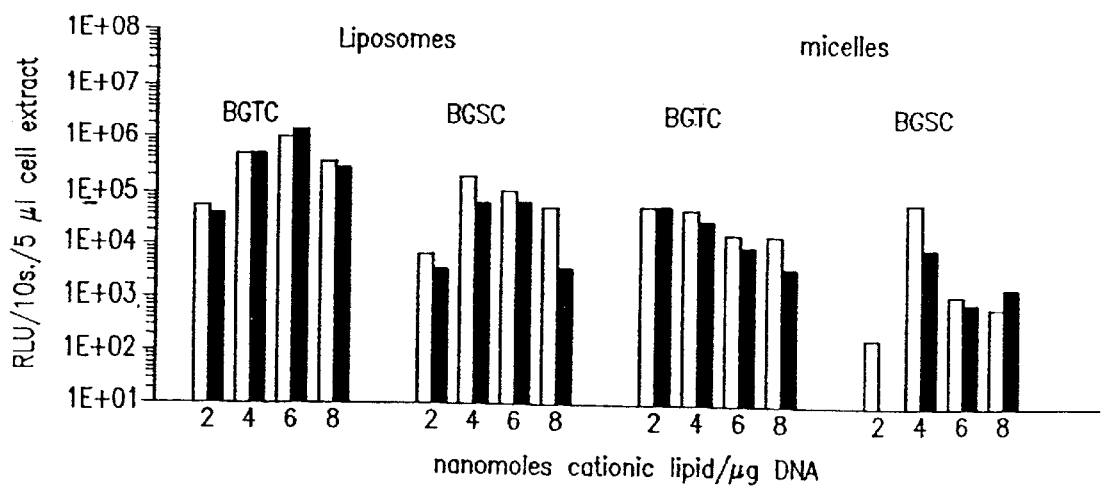
Figure 5C:
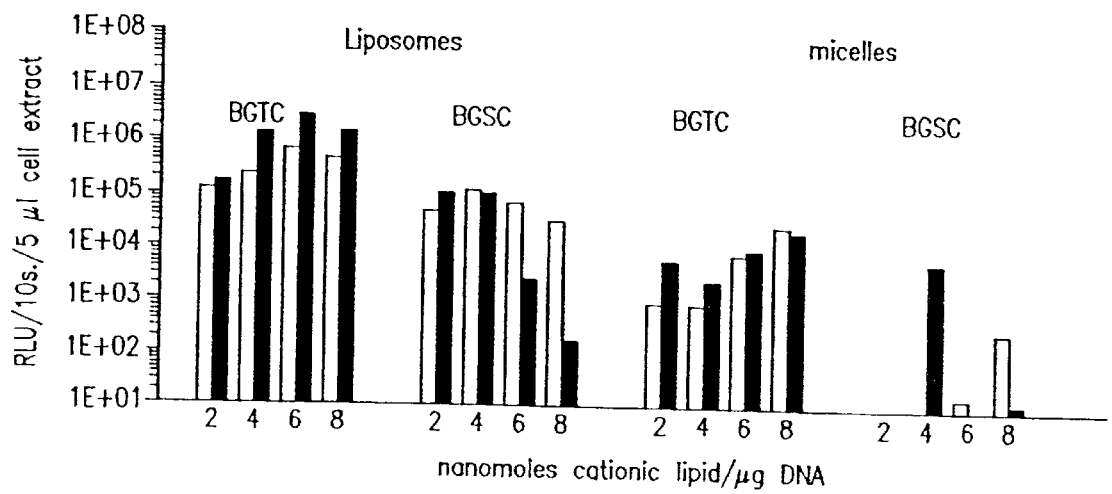
Figure 5D:
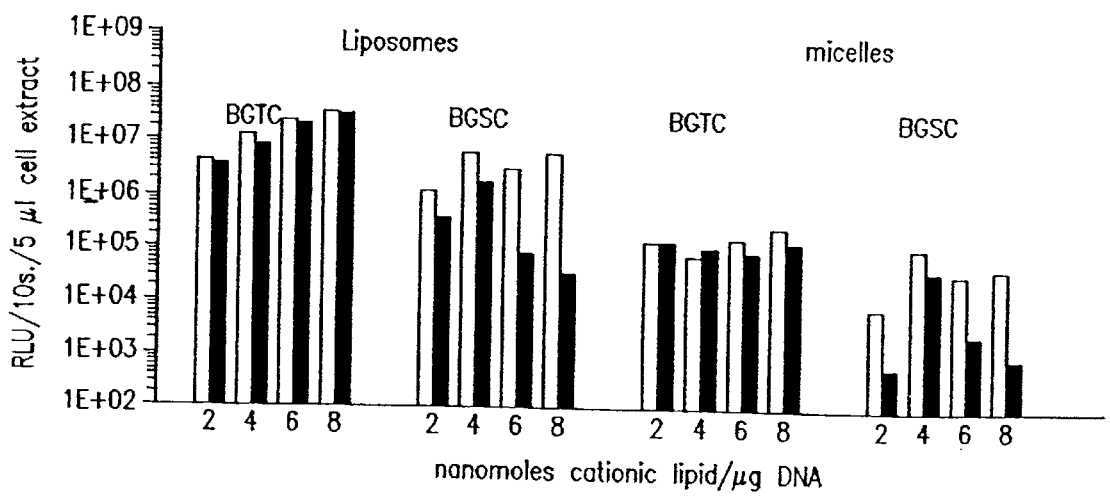

FIG. 4: Measurement of the transfection efficiency as a function of the total lipids/DNA ratio.

FIGS. 5A–5D: Measurement of the serum effect on the transfection efficiency of HepG2 (5A), HeLa (5B), NIH 3T3 (5C) and 293 (5D) cells. Shaded bars: presence of serum; open bars: transfections in the absence of serum for 2 h.

FIGS. 6A–6E: Photographs of cryosections of murine tracheae showing reporter gene expression in the epithelium of the respiratory tract after in vivo transfection with BGTC/DOPE liposomes. (6A) and (6B): detection of the expression of beta-galactosidase in transfected cells located at the surface of the epithelium (6A) and in the submucosal glands (6B); (6C): detection of the cells expressing beta-galactosidase in the submucosal glands by immunoperoxidase labelling using an anti-beta-galactosidase monoclonal antibody; (6D): detection of the cells expressing luciferase in the submucosal glands by immunoperoxidase labelling using an anti-luciferase polyclonal antibody; (6E): immunoperoxidase staining: negative control carried out in the absence of antibodies.

Figure 7:
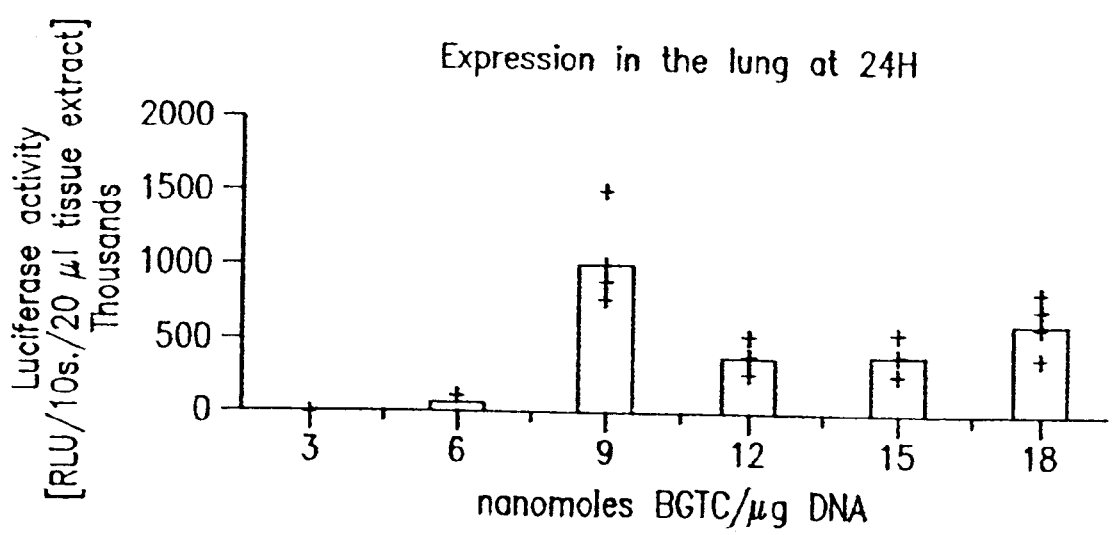

FIG. 7: Measurement of the transfer efficiency of genes in vivo by intravenous injection of a DNA/BGTC-liposome complex.

Figure 8A:
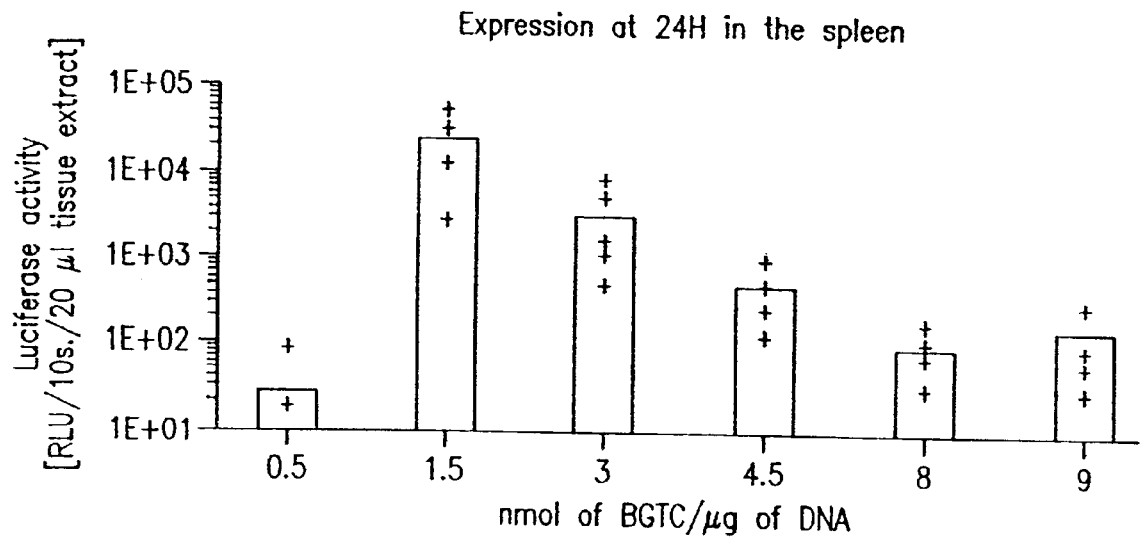
Figure 8B:
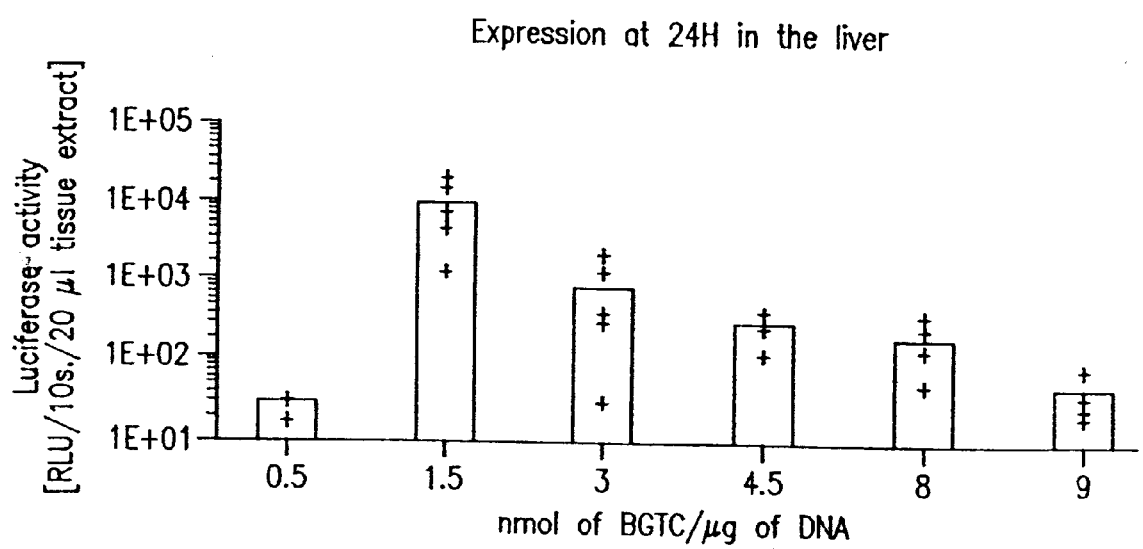

FIGS. 8A–8B: Measurement of the transfer efficiency of genes in vivo by intraperitoneal injection of a DNA/BGTC-liposome complex.

A—PREPARATION OF DERIVATIVES ACCORDING TO THE INVENTION

MATERIALS AND METHODS

1. Physical measurements

The proton nuclear magnetic resonance spectra (1H NMR) were recorded on a Bruker AC200 spectrometer. The chemical shifts are expressed in ppm relative to TMS.

2. Chromatographies on silica

The thin-layer chromatographies (TLC) were carried out on Merck silica gel plates 0.2 mm thick Column chromatographies were carried out on Merck silica gel 60 of particle size distribution 0.040–0.063 mm.

EXAMPLE 1

PREPARATION OF GUANIDINO SPERMIDINE CHOLESTEROL BGSC

1; Preparation of the Di-Boc carbamate (1)

A solution of cholesteryl chloroformate (0.9 g, 2 mmol) and $Et_3N$ (0.214 g, 2 mmol) in $CH_2Cl_2$ (40 ml) is added to a solution of $^1N, ^8N$-Boc-$_2$-spermidine (0.690 g, 2 mmol) in $CH_2Cl_2$ (20 ml). After refluxing for 5 hours, the mixture is washed with water (2×50 ml), dried over $Na_2SO_4$ and the solvent is evaporated off. The crude product is purified by chromatography on a silica gel using $CH_2Cl_2$/MeOH 95/5 as eluent to give pure carbamate (1.3 g, 86%).

$^1H$ NMR $\delta(CDCl_3, 200\ Mhz)$; 0.5–2.5 (m, structure of cholesteryl, Boc signal and central CH2 groups from spermidine), 3.1–3.3 (m, 8H, N—$CH_2$), 4.50 (m, 1H, $H_{3\alpha}$), 5.37 (d, 1H, $H_6$).

2. Preparation of the aminocarbamate (2)

Compound (1) (1.3 g) is dissolved in 20 ml of $CH_2Cl_2$ and 2 ml of freshly distilled $CF_3CO_2H$ are added to this cooled solution (ice bed) in order to release the protective BOC groups. After stirring at room temperature for 3 hours. 50 ml of $^1N$ NaOH are added and the mixture is extracted with $CH_2Cl_2$ The organic layers are washed with water, dried over $Na_2SO_4$ and evaporated so as to obtain the crude aminocarbamate (2) (0.945 g, 98%).

$^1H$ NMR, $\delta(CDCl_3, 200\ Mhz)$; 0.5–2.5 (m, structure of cholesteryl and central groups from spermidine), 2.7 (m, 4H, $CH_2$—N—C0—), 3.25 (broad m, 4H, N—$CH_2$), 4.49 (m, 1H, $H_{3\alpha}$), 5.35 (d, 1H, $H_6$).

3.—Synthesis of BGSC.

The crude carbamate (2) (0.94 g) is dissolved in 30 ml of THF/MeOH 85/15. Next, 1H-pyrazolecarboxamidine (0.495 g, 3.4 mmol) and diisopropylethylamine (0.436, 3.4 mmol) in 30 ml of THF/MeOH 85/15 are added. After stirring at room temperature for 18 hours, 250 ml of diethyl ether are slowly added and the precipitate obtained is separated by decantation. The crude compound is suspended three times in diethyl ether and separated by decantation to give pure GSC (0.570 g, 47%).

1H NMR $\delta$(DMSO d6) 200 MHz; 0.5–2.5 (m, structure of cholesteryl and central $CH_2$), 3.1 (m, 8H, N—$CH_2$), 4.3 (m, 1H, $H_{3\alpha}$), 5.3 (d, 1H, $H_6$); 7.2 (broad s, 8H, $NH_{2+}$), 7.8 (s, 2H, NH), Anal. Calc. for $C_{37}H_{67}N_7O_2.2HCl$, C, 62.15; H, 9.67; N, 13.71

Result of element analysis: C, 62.28; H, 9.81; N, 13.15

EXAMPLE 2

PREPARATION OF GUANIDINO TREN CHOLESTEROL, BGTC 1. preparation of Aminocarbamate (5)

A solution of cholesteryl chloroformate (1.8 g, 4 mmol) in 100 ml of $CH_2Cl_2$ is slowly added to a saturation of tris (2-aminoethyl)amine (TREN) (11.68 g, 80 mmol) in 400 ml of $CH_2Cl_2$. After stirring at room temperature for two hours, the inert amine is released by washing with water (3×100 ml) and after dying over $Na_2SO_4$, the solvent is evaporated off. (5) is isolated in the trihydrochloride form in the following manner: the crude product is dissolved in 10 ml of MeOH and a saturated methanolic HCl solution (5 ml) is added dropwise; the precipitate obtained is separated by decantation and, to obtain a pure compoud, is suspended three times in MeOH and separated by decantation. After drying under vacuum, the pure trihydrochloride (6) is obtained (1.71 g, 64%).

1H NMR $\delta(CDCl_3—\epsilon CD_3OD, 200\ MHz)$, 0.5–2.4 (m, structure of cholesteryl, 2.5 (m, 2H, $CH_2NHCO$), 2.8 (broad s, 4H, +HN—$CH_2$), 3.06 (broad s, 4H, $CH_2NH_3+$), 3.20 (m, 2H, $^\oplus HN$—$CH_2$), 4.4 (m, 1H, $H_{3\alpha}$), 5.3 (d, 1H, $H_6$), Anal. Calc. for $C_{34}H_{62}N_4O_2$. 3HCl; C, 61.10; H, 9.80; N, 8.38. Result: C, 61.25; H, 9.96; N, 8.22.

2—Preparation of B.GTC

A solution of cholesteryl chloroformate (2.24 g, 5 mmol) in 100 ml of $CH_2Cl_2$ is slowly added to a broad saturation of tris (2-aminoethyl)amine (TREN) (29.2 g, 200 mmol) in 250 ml of $CH_2Cl_2$. After stirring at room temperature for 2 hours, the inert amine is released by washing with water (3×100 ml) and after drying over $Na_2SO_4$, the solvent is evaporated off. The crude product (3.2 g) is dissolved in THF/MeOH 50/50 (20 ml); next, 1H-pyrazole-1-carboximidine (1.495 g, 10 mmol) and diisopropylamine (1.3 g, 10 mmol) are added to the mixture. After stirring at room temperature for 18 hours, diethyl ether is added and the precipitate obtained is separated by decantation. To obtain a pure sample, the crude compound is suspended three times in diethyl ether and separated by decantation (2.15 g), 60% after drying under vacuum.

1H NMR (DMSO d6, 200 MHz); 0.5–2 (m, structure of cholesteryl), 2.2 (m, 2H, N—$CH_2$), 2.6 (broad, s, 4H, N—$CH_2$), 3.0 (d, 2H, N—$CH_2$), 3.2 (broad, s, 4H), 4.3 (m, 1H, $H_{3\alpha}$), 5.3 (d, 1H, $H_6$), 7.3 (broad, s, 8H, $NH_2+$), (7.8 (broad s, 2H, NH). Anal. Calc. for $C_{36}H_{66}N_8O_2.2HCl$; C, 60.39; H, 9.57; N, 15.65. Result: C, 60.38; H, 9.67; N, 15.56.

EXAMPLE 3

PREPARATION OF BIS AMIDINIUM BISHYDROCHLORIDE BACD

1. Preparation of the dinitrile

A solution of cholesteryl chloroformate (8.97 g; 20 mmol) in $CH_2Cl_2$ (100 ml) is added dropwise to a solution of iminopropionitrile (2.46 g, 20 mmol) and $Et_3N$ (2.02 g, 20 mmol in $CH_2Cl_2$ (100 ml). After stirring at room temperature for 6 hours, the mixture is washed with water (2×100 ml) and dried over $Na_2SO_4$. The solvent is evaporated off and the crude product (10.5 g) is recrystallized from methanol. (8.59 g; 80%).

1H NMR $\delta(CDCl_3, 200\ MHz)$. 0.5–2.5 (m, structure of cholesteryl), 2.7 (m, 4H; —$CH_2CN$), 3.62 (m, 4H, —CH2—N—), 4.50 (m, 1H, $H_{3\alpha}$), 5.39 (d, 1H, $H_6$).

2. Preparation of the dithioamide

A slight $H_2S$ stream is bubbled for 2 hours through a solution of the dinitrile prepared as described above (0.324 g, 6 mmol) and diethylamine (0.884 g; 12 mmol) in DMF (30 ml), maintained at 50° C. The blue solution is poured over ice and the precipitate thus obtained is separated by filtration. This crude product is dissolved in $CH_2Cl_2$ and washed with water (2×50 ml). After drying over $Na_2SO_4$, the solvent is evaporated off and the product obtained recrystallized twice from methanol (1.86 g; 51.5%).

1H NMR (DMSO d6, 200 MHz); 0.5–2.5 (m, structure of cholesteryl), 2.67 (t, 4H, N—$CH_2$), 3.50 (t, 4H, S=C—$CH_2$), 4.3 (m, 1H, $H_{3\alpha}$), 5.33 (d, 1H, $H_6$).

3. Preparation of the dithioamidate bisiodide

Methyl iodide (2 ml) is added to a solution of dithioamide (0.603 g; 1 mmol) in acetone (20 ml) and the mixture is allowed to stand at room temperature for 48 hours. The precipitate obtained is filtered (0.741 g; 83.5%). This product is used directly without further purification.

4. Preparation of bis amidinium bishydrochloride BADC.

An $NH_3$ stream is bubbled for 2 hours through a suspension at the reflux temperature of bisiodide (0.741 g; 0.83 mmol), as obtained previously, in isopropanol (10 ml) and then the heating under reflux is continued for an additional 4 hours. The isopropanol is evaporated off and the residue is taken up in methanol (10 ml). After passing this solution over a basic ion-exchange resin, a hydrochloric acid stream is passed through the eluent and the solution is evaporated to dryness. The bishydrochloride thus obtained is dissolved in a minimum of ethanol (about 5 ml). A light insoluble matter is filtered off and a large excess of diethyl ether is added to the filtrate. A powder is obtained which is filtered and dried (320 mg; 60%). Recrystallization from isopropanol makes it possible to isolate the expected product, in an analytically pure form.

1H NMR (DMSO d6, 200 MHz); 0.5–2.6 (m, structure of cholesteryl and —$CH_2$-amidinium), 3.57 (s, broad 4H, N—$CH_2$) 4.3 (m, 1H, $H_{3\alpha}$), 5.3 (d, 1H, $H_6$), 8.64 (s, broad; 2H; $NH_2$), 9.07 (s; broad; 1H; NH), 9.18 (s; broad; 2H).

Anal. Cal. for $C_{34}H_{56}N_4O_2 \cdot 2HCl$: C, 65.25. H, 9.32; N, 8.94. Result C, 65.40. H, 9.87; N, 9.55.

B: USE OF DERIVATIVES ACCORDING TO THE INVENTION FOR THE IN VITRO AND IN VIVO TRANSFER OF GENES MATERIALS AND METHODS

1—The transfection trials below are carried out with BGSC and BGTC prepared according to the protocols described in Examples 1 and 2.

2—Preparation of the liposomes

A mixture of cationic lipid and DOPE (in a molar ratio of 3/2 ) in chloroform ($CHCl_3$) is evaporated under vacuum and resuspended in a 20 mM HEPES buffer solution at PH 7.4, under an N2 atmosphere.

The final lipid concentration is 1.2 mg/ml.

The mixture is vortexed for 5 min and then "sonicated" for 5 min with a sonicator (Branson Ultrasonic 2210), finally stored at +4° C. for 24 h for hydration.

The resulting dispersion is again "sonicated" (Sonifier Branson 450) for 5 to 10 mm to form liposomes.

After centrifugation, the solution is filtered on a filter of pore diameter 0.22 µ(millex GS, Millepore) and stored at +4° C.

The size of the liposomes containing BGSC or BGTC was studied with the aid of a laser diffraction apparatus (Autosizer 4700, Malvern Instruments). This study shows a single peak corresponding to a mean diameter of 50 nm in number multimodal analysis.

3—Cell cultures

The source (species and tissues) of most of the cell lines used for the transfection experiments is given in Table I.

The cells of the HeLa cell (P Briand, ICGM Paris) are derived from a human carcinoma of cervical epithelial origin.

The NIH 3T3 cells (C Lagrou, Institut Pasteur, Lille) are mouse fibroblasts.

The NB2A cell line (C. Gouget, Paris) is derived from a mouse neuroblastoma.

All the cells, with the exception of the AtT-20 and PC12 cells, were cultured in Dulbecco's modified medium (DNEM, GIBCO) supplemented with 10% foetal calf serum (FCS; GIBCO), penicillin at 100 units/ml (GIBCO) and streptomycin (GIBCO) at 100 µg/ml.

The AtT-20 cells were cultured in DMEM/F12 (GIBCO) supplemented with 10% foetal calf serum.

The PC12 cells were cultured in DMEM supplemented with 10% FCS and 5% horse serum.

All the cells were maintained in culture in plastic dishes (Falcon) under a humid atmosphere with 5% CO2.

4—Plasmids

The plasmids pRSV-Luc (O. BENSAUDE, ENS, Paris) and pRSV-nlsLacZ were amplified in E. coli and prepared by purification on CsCl gradient by standard techniques. In the plasmid pRSV-nlsLacZ and the plasmid pRSV-Luc, the E. coli LacZ gene and its nuclear localization signal sequence and the luciferase gene are respectively under the transcriptional control of the LTR/RSV (Rous Sarcoma Virus). Plasmid pXL2774 comprises the gene encoding luciferase under the control of the cytomegalovirus (CMV) promoter.

5—Protocol for in vitro transfection

On the day before the transfection, $2 \times 10^5$ cells are deposited per well (Falcon 6-well plates).

Each well contains a different cell line.

Thus, on the day of the transfection, the cells are semi-confluent.

The plasmid DNA (5 µg) and the desired quantity of bis-guanidinium lipid were each diluted in 250 µl of FCS-free DMEM and vortexed. After about 5 min, the two solutions were left to incubate at room temperature of 15 min. The transfection mixture is then added to the cells (0.5 ml per well) which were washed with a serum-free medium. After 4 to 6 hours of incubation at 37° C., 1 ml of medium with serum is added to each well without removing the transfection mixture. 24 hours after the transfection, the medium is replaced with 1 ml of fresh culture medium. The cells are collected 2 days after the transfection to measure the expression of luciferase.

Control transfections were performed using commercially available transfection agents:

the lipopolyamine Transfectam® (JP Behr, Strasbourg, France) was used in alcoholic solution at an optimum Transfectam®/DNA ionic charge ratio 6–8.

Lipofectin® (Life Technologies Inc., Cergy Pontoise, France) which is a liposome formulation having, as neutral lipid, DOPE and, as cathionic lipid, DOTMA. (N[1(2,3-dioleyloxy)propyl]-N,N,N-trimethylammonium chloride).

The DNA/Liposome complexes were obtained under the standard conditions recommended by the manufacturer.

cells were transfected by calcium phosphate precipitation. (Keown, W. A., Campbell, C. R.; Kucherlapati, R. S. (1990) *Methods in Enzymology;* Academic Press: New York, 185, 527–537).

6—Measurement of luciferase for the transfections carried out in vitro

The luciferase activity is measured 48 hours after transfection using a variant the procedure of De Wet et al. (De Wet, J. R., Wood, K. V., DeLuca, M., Helinski, D. R. & Subramani, S. (1987) *Mol. Cell. Biol.* 7, 725–737.)

the culture medium is removed the cells are washed with a saline solution of cold phosphate buffer then they are lysed by incubation in 250 μl of lysis buffer (25 mM triphosphate pH 7; 8.8 mM MgCl$_2$, 1 mM dithiotreitol, 15% glycerol and 1 % triton X-100).

a clear lysate is obtained after removal of the insoluble materials by centrifugation (15 mm a +4° C.) in a microcentrifuge.

an Aliquot (20 μl) of cell extract is diluted in 100 μl of lysis buffer to which 9 μl of 25 mM ATP (sigma) and 20 μl of 25 mM luciferin (sigma) are added.

the samples are placed in a luminometer (Lurmet LB9501 Berthold, Nashua, NH) and the light emission is measured for 10 seconds.

The calibration of the RLU/Luciferase curve was carried out using various dilutions of purified firefly luciferase (sigma) and shows that the linear portion of the curve goes from $10^4$ a $10^7$ RLU (relative light units).

The protein concentration was measured by the BCA (bicinchoninic acid) test using bovine serum albumin as control.

The data for the luciferase activity are expressed in RLU/mg of protein.

7—Protocol for in vivo injection at the level of mouse respiratory tracts

The mice used are male OF1 mice (weight 30 ) obtained from Iffa-Credo (Lyon, France). Cationic liposomes BGTC/DOPE (molar ratio 3:2) are used. The transfection mixture is obtained from 10 μg of plasmid DNA (in 10 μl water), 20 μl of cationic liposomes in a 20 mM Hepes medium (pH 7.4), at a total lipid concentration of 5 mg/ml. The DNA/lip aggregates thus formed have a charge ratio of the order of 6.

After anaesthetizing the mice with pentobarbital, the transfection mixture (30 μl) is injected into the respiratory tracts by intratracheal instillation via a cannula inserted into the tracheal lumen. 48 h after the instillation, the animals are sacrificed by pentobarbital overdoes and the lungs and tracheae removed for analysis.

8—X-gal staining

To measure the expression of E. coli beta-galactosidase in the primary cultures, the cells are impregnated for 15 minutes at 4° C. with a 4% paraformaldehyde solution and they are then incubated with chromogenic beta-galactosidase substrate X-gal (Sigma). The blue colour of the nuclei of the transfected cells is measured by luminescence microscopy.

9—Measurement of X-gal cells at the level of the respiratory tracts transfected in vivo For the detection of X-gal cells at the level of the respiratory tracts, the lungs and tracheae are treated for 1 h in 4% paraformaldehyde, then immersed overnight in PBS containing 30% sucrose, then incorporated into a freezing medium and frozen with liquid nitrogen. Cryostat sections of 5 μ are then stained for β-galactosidase activity by incubating overnight with the X-gal reagent (Sigma).

10—Measurement of luciferase at the level of the respiratory tracts transfected in vivo To measure the luciferase activity at the end of the in vivo transfections, tissue fragments are exposed to 30 μl of lysis buffer (25 mM Tris-phosphate pH 7.8, 1 mM dithiothreitol (DTT), 15% glycerol and 1% Triton X-100), lysed in about 1 min with a homogenizer (Polylabo, Strasbourg, France) and stored on ice. After centrifugation, 20 μl of lysate is used for the measurement. The luciferase activity is expressed in RLU per mg of protein.

11—Immunochistochemical protocol

Cryosections of lung and trachea samples are incubated for 1 h with either murine monoclonal antibodies anti-*E. coli* β-galactosidase at 5 μg/ml (Genzyme, Cambridge, Mass.) or rabbit polyclonal antibodies 1:400 dilution (Promega).

The Escherichia coli β-galactosidase protein is measured by staining with immunoperoxidase using a biotin-labelled secondary antibody anti-mouse Ig (Boehringer) and a streptavidin-POD conjugate (Boehringer). The luciferase protein is measured by staining with immunoperoxidase using an anti-rabbit goat antibody (ICN Biomedicals, Inc) and the rabbit peroxidase-antiperoxidase (PAP) system (Dako Glostrup, Denmark). The sections are examined by luminescent microscopy. Negative controls are performed without antibodies.

EXAMPLE 4

Transfections In Vitro at Different Transfection AGENT/DNA Ratios

In order to optimize the transfection efficiency obtained with BGTC/DNA aggregates, the applicant studied the influence of the BGTC/DNA ratio on the transfection rate in 3 different types of mammalian cells known for their relative sensitivity to conventional transfection methods. The results are presented in FIG. 3.

Transfection experiments were thus carried out with murine fibroblasts 3T3 human epithelial cells HeLa and mouse neuroblastomas NB2A. During these experiments, a certain fixed quantity of plasmid pRSV-Luc was brought into contact with variable quantities of BGTCin solution. To determine the ratio range to be studies, the applicant started out from the principle that one μg of DNA is equivalent to 3 nm of negatively charged phosphate and that only two guanidinium groups are positively charged at neutral pH for formation of the aggregates and for transfection. The luciferase activity is measured 48 h after the transfection. The expression of luciferase is maximum for aggregates containing 6 (HeLa cells) to 8 (3T3 and NB2A cells) guanidinium groups for one phosphate group of DNA, that is to say aggregates having a high positive charge.

EXAMPLE 5

Transfections In Vitro with Different Cell Types

The transfer of genes by the intermediacy of cationic lipids is an attractive transfection technique not only because it does not require intermediates but also because it makes it possible to transfect a very wide variety of cells of different tissues and organisms. To study the extent of the efficiency of BGTC as transfection agent, several cell lines of various origins were tested. The results are presented in Table 1 below. The charge ratio was chosen between 6 and 8 for a maximum efficiency. To establish a comparison, cells of the same lines were also transfected using a lipopolyamine, on the one hand, and calcium phosphate on the other. The results show that BGTC is normally as effective as Transfectam and twice as effective as calcium phosphate. Table 1: Expression of luciferase in various mammalian cell lines transfected either with BGTC, calcium phosphate or Transfectam®

| Species | Cell lines | Tissues | RLU/mg of cellular proteins | | |
|---------|-----------|---------|------|------|------|
| | | | BGTC | Calcium phosphate | Transfectam ® |
| Human | A549 | Lung carcinoma | $4 \times 10^5$ | $7 \times 10^3$ | $3.1 \times 10^5$ |
| Monkey | COS-7 | Kidney transformed with SV40 | $2.1 \times 10^7$ | $3.7 \times 10^5$ | $6.4 \times 10^6$ |
| Dog | MDCK-1 | Kidney | $3 \times 10^6$ | $4.5 \times 10^5$ | $2.2 \times 10^6$ |
| Rat | RIN-m5F | Pancreatic islet tumour cell | $2 \times 10^7$ | $2 \times 10^5$ | $3.3 \times 10^5$ |
| | ROS | Osteosarcoma | $4.0 \times 10^6$ | $4.5 \times 10^5$ | $2.3 \times 10^6$ |
| | PC12 | Pheochromocytoma | $3 \times 10^7$ | $1.7 \times 10^5$ | $6 \times 10^6$ |
| Mouse | AtT-20 | Pituitary tumour | $2 \times 10^7$ | $8 \times 10^5$ | $3 \times 10^7$ |

All the transfections were performed at least twice (n≧2).

EXAMPLE 6

Transfections In Vitro in the Presence of a Neutral Lipid

The compound BGSC being less soluble in aqueous medium than BGTC, the applicant used the former in the form of liposomes in the presence of a neutral lipid DOPE (dioleoylphosphatidylethanolamine). The formulations are prepared in a 3/2 molar ratio. A second preparation containing, this time, BGTC was also prepared with DOPE under the same conditions.

6.1—Determination of the total lipid/DNA ratio

The applicant first determined the lipid/DNA ratio during a transfection experiment on HeLa cells. The curve obtained is represented FIG. 4. The transfection optima are obtained for BGSC liposomes/DNA ratios of between 1.5 and 5 with a centre at 2.5–3. The guanidinium groups being protonated at neutral pH, the best BGSC-DOPE/DNA aggregates have a positive charge of about 3 (FIG. 4).

The best BGSC-DOPE/DNA ratios are therefore less than those obtained with aggregates of the BGTC/DNA type (between 6 and 8). Transfection in the presence of cationic liposomes is facilitated by the presence of DOPE and the fusogenic properties thereof.

6.2—Transfection of different cell lines by cationic liposomes

The applicant carried out transfection experiments in different cell lines using formulations of cationic liposomes BGSC-DOPE and BGTC-DOPE in 3/2 molar ratios. The guanidinium of the lipids/phosphates of the DNA charge ratio is about 2.5 (−3) for these two gene transfer systems. A transfection with Lipofectin® serves as control. The results are presented in Table 2 below.

These results show that the cholesterol derivatives carrying guanidinium groups in the form of cationic liposomes are at least as effective for transfection as Lipofectin. These results can of course be optimized for each cell line.

TABLE 2

Expression of luciferase in different eukaryotic cell lines transfected by means of BGSC/DOPE liposomes, of BGTC/DOPE liposomes and of Lipofectin ®

| Cell lines | RLU/mg of cellular proteins | | |
|-----------|------|------|------|
| | BGSC liposomes | BGTC liposomes | Lipofectin ® |
| HeLa | $4.6 \times 10^6$ | $7.7 \times 10^6$ | $3.3 \times 10^6$ |
| A 549 | $6 \times 10^5$ | $2 \times 10^5$ | $4 \times 10^6$ |
| COS-7 | ND | $1.4 \times 10^7$ | $9.5 \times 10^6$ |
| MDCK-1 | $1 \times 10^6$ | $7 \times 10^6$ | $1.9 \times 10^6$ |
| ROS | ND | $9 \times 10^6$ | $6 \times 10^6$ |
| NB2 A[a] | $1.5 \times 10^7$ | $1.4 \times 10^7$ | ND |
| NIH 3T3[a] | $7 \times 10^6$ | $1.5 \times 10^6$ | ND |

All the transfections were performed at least three times (N≧3).

[a]: mean measurement in RLU of the luciferase activity for 100 μg/500 μg of total lysate (n≧4).

EXAMPLE 7

Study of the Effect of the Presence of Serum Proteins on the Gene Transfer Efficiency In Vitro Most of the transfection compositions based on cationic lipids have a reduced efficiency in the presence of serum. The aim of this example is to test the sensitivity of the compounds of the invention to the serum effect.

7.1—Formulations of cationic lipids

The lipids described in the invention are solubilized in ethanol.

i) Solutions of "liposomes" are obtained in the presence of DOPE as follows: DOPE (AVANTI) in solution in chloroform is added to the lipid solutions in ethanol, in a cationic lipid/DOPE molar ratio of 3/2. After evaporation to dryness, the mixtures are taken up in water and heated at 50° C. for 30 minutes;

ii) solutions of "micelles" are obtained according to the protocol described for the production of "liposomes" but the solution of DOPE is replaced with chloroform.

The solutions are all adjusted to 10 mM cationic lipid.

7.2—Nucleic acid

The nucleic acid used is the plasmid pXL2774.

7.3—Cytofectant mixtures (preparation immediately before use)

The DNA is diluted to 20 μg/ml in 150 mM NaCl and the different formulations of cationic lipid are diluted in water to 40, 80, 120 and 160 μM. The solutions of DNA and lipid are mixed volume for volume, giving ratios in nmol/μg DNA of 2, 4, 6 and 8, respectively; the saline concentration is 75 mM 7.4—Transfections The cells are cultured under appropriate conditions in 24-well microplates (2 cm²/well) and are transfected while still in the exponential growth phase and are 50–70% confluent. The cells are washed with twice 500 μl of medium free of serum proteins and grown again either in serum-free medium [transfection in the absence of serum], or in complete medium [transfection in the presence of serum] and 50 μl of cytofectant mixture [0.5 μg DNA/well] are added to the cells [3 wells/condition lipid-DNA].

When the cells are transfected in "absence of serum", the growth medium is supplemented with the appropriate quantity of serum 2 hours after the transfection.

The transfection efficiency is evaluated by measurement of the expression of luciferase according to the recommendations given for the use of the Promega kit [Luciferase Assay System]. The toxicity of the cytofectant mixtures is estimated by measurement of the protein concentrations in the cell lysates.

7.5—Results (FIG. 5)

The results obtained with four cell types [NIH3T3—293—HepG2—HeLa] show that, under the conditions tested, the formulations in the form of "liposomes" are more effective than those in the form of "micelles". Moreover, in contrast to what is observed with most of the cytofectant preparations containing cationic lipids, no significant inhibitory effect linked to the presence of serum for BGTC in the form of "liposomes" or of "micelles" could be demonstrated under our transfection conditions.

EXAMPLE 8

In Vivo Expression of Transgene in Mouse Respiratory Tracts with BGTC/DOPE Liposomes To do this, we used the cationic liposomes BGTC/DOPE. The production of DNA/liposomes aggregates and the administration protocol are performed as described in material and methods.

The X-gal cells are detected in the epithelium of the respiratory tracts of the treated mice 48 h after transfection into the cells of the LacZ plasmid with the aid of the BGTC/DOPE liposomes. The results are presented in FIG. 6.

Most of the transfected cells are located in the trachea and only a few X-gal cells are observed in the secondary respiratory tracts. This type of distribution has already been reported in other cellular transfections.

Figure 6A:
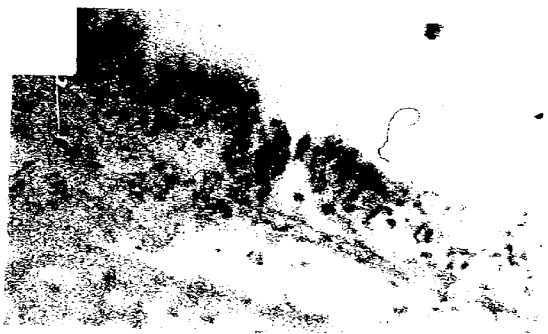
Figure 6B:
Figure 6C:
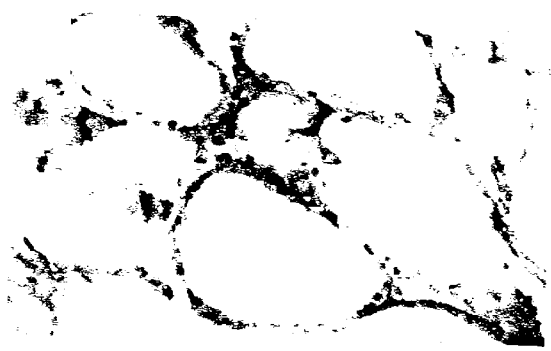
Figure 6D:

An immunohistochemistry was, in addition, performed in order to identify the product of the reporter gene. Predominantly, it is the mature cells which are transfected at the level of the surface of the epithelium (FIG. 6A). These date show that the cationic liposomes are capable of inducing the transfection of genes in nonproliferative and completely differentiated cells of the epithelium of the respiratory tracts. The expression of the transgene is also detected in the submucosal glands (FIG. 6B). The detection by immunological labelling of the transfected cells, using a monoclonal antibody directed against $E.\ coli$ β-galactosidase confirms this expression in the submucosal glands and the surface epithelium (FIG. 6D). Transgenic expression is also demonstrated in the submucosal glands by immunoperoxidase staining with an antibody directed against the luciferase protein after transfection of pRSV-Luc with BGTC/DOP (FIG. 6D).

Figure 6E:

Negative controls were performed without antibody (FIG. 6E).

These results are of a very special interest for gene therapy directed against cystic fibrosis. Indeed, to treat this pathology, it is necessary to target the submucosal glands which are the principal site of expression of CFTR in the human bronchi.

EXAMPLE 9

Quantitative Measurement of the Transfection Efficiency of BGTC/DOPE In Vivo

To do this, the lungs and the trachea of mice, treated with BGTC/DOPE liposome and plasmid pRSV-Luc under the conditions described in Example 8 are removed 48 h after transfection and the luciferase activity measured according to the protocol described in material and method.

The results are presented in Table 3 below.

TABLE 3

| VECTORS | LUCIFERASE ACTIVITY (RLU/mg protein) |
|---|---|
| BGTC/DOPE liposomes: | |
| pRSV-Luc | $2.8 \times 10^5$ (mean: $3 \times 10^4 - 8 \times 10^5$) |
| pRSV-Lac Z | 0 |
| Naked DNA | |
| pRSV-Luc | 0 |

The luciferase activity is detected systematically in trachea homogenates but not in lung homogenates. This observation is in agreement with the previous results obtained during examination of the distribution of the cells positive to X-gal. It can be noted that the luciferase expression is directly linked to the expression plasmid since no activity could be detected in the control containing a LacZ plasmid. As a control, it was also a transfection of the plasmid was carried out without vector. No luciferase expression is observed in this control assay.

These date demonstrate the efficiency of the BGTC/DOPE liposomes for in vivo gene transfection in the respiratory tracts.

EXAMPLE 10

Gene Transfer In Vivo by Intravenous or Intraperitoneal Injection

The formulations of cationic lipids and DNA are described in Example 7.

10.1—Dose Effect of the cationic lipids (FIGS. 7–8)

5-week-old BalbC mice are injected via the intravenous (tail vein) or intraperitoneal route with 200 µl of transfecting mixture in solution in 37.5 mM NaCl, 5% glucose and the expression of luciferase is determined 24 hours post-transfection in the lung after intravenous injection, and in the liver and the spleen after intraperitoneal injection. The organs are removed in the cold in lysis buffer [Promega E153A] supplemented with protease inhibitors [Boehringer 1697498] and homogenized with a Heidolph DIAX600 grinder. The luciferase activity is determined in the 14000 g supernatant of the tissue extracts.

Intravenous injection

Each mouse receives 50 µg of DNA complexed with various concentrations of BGTC in the form of "liposomes". The optimum ratio in nanomoles cationic lipid/µg DNA observed is 9 (FIG. 7); no toxicity could be detected for doses of up to 900 nanomoles of BGTC injected.

Intraperitoneal injection

BGTC in the form of "liposomes" was injected with 100 µg of DNA per mouse. Both in the liver (FIG. 8B) and in the spleen (FIG. 8A), the maximum expression is obtained for 1.5 nanomoles BGTC/µg of DNA.

10.2—Kinetics of expression after intravenous injection

We determined the biodistribution of the expression of luciferase in 7 organs as a function of time following the injection of 200 µl of BGTC "liposomes"/DNA mixture in 37.5 mM NaCl, 5% glucose [50 µg DNA and 9 nanomoles BGTC/µg DNA] into the tail vein of 5-week old BalbC mice. The results are expressed in picograms of luciferase extracted per organ based on a calibration curve with luciferase marketed in crystallized form. The limit of detection is between 0.5 and 1 picogram of luciferase.

We have demonstrated that, under the conditions tested, the maximum expression is obtained 23 hours post-transfection for 6 of the 7 organs studies, namely the diaphragm, the gastrocnemius, the heart, the lung, the kidney and the spleen. The expression at the level of the liver appears to be more premature. The maximum expression is obtained at the pulmonary level with a level of 0.5 nanogram at 23 hours post-transfection.

What is claimed is:

1. A compound of general formula I or a salt thereof

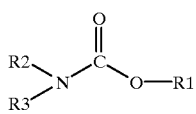

in which:
R1 represents a cholesterol derivative or an alkylamino —NR'R" group, with R' and R" independently representing a saturated or unsaturated, linear or branched $C_{12}$ to $C_{22}$ aliphatic radical;
R2 and R3 independently represent hydrogen or a group of general formula II with at least one of R2 and R3 being different from hydrogen,

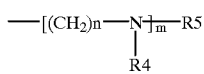

in which:
n and m independently represent an integer between 0 and 4 and are distinct between the groups R2 and R3; and
R4 and R5 independently represent hydrogen or a group of formula III:

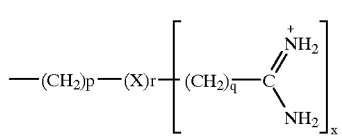

in which p and q independently represent an integer from 0 to 4 and r is equal to 0 or 1, with the following conditions: (A) when r is equal to 1, (1) X represents an NH group and x is equal to 1 or (2) X represents nitrogen and x is equal to 2; (B) it is possible for p, q and r to vary independently between the groups R4 and R5; (C) at least one of R4 or R5 is different from hydrogen; and (D), when R1 is a cholesterol derivative, n is 4, m is 1, one of R2 or R3 is hydrogen, and one of R4 or R5 is hydrogen; R4 or R5, whichever is not hydrogen, is not a group of formula III in which p, r, and q are equal to 0 and x is equal to 1.

2. The compound according to claim 1 in which R2 and R3 independently represent hydrogen or a group of general formula IV:

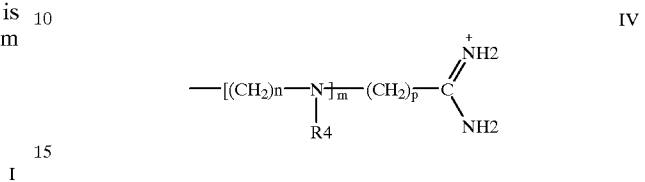

in which n, m and p are as defined in claim 1 and R4 represents hydrogen or a group of formula V:

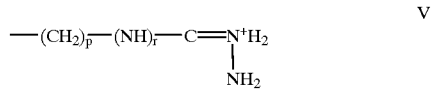

with q and r as defined in claim 1, and it being possible for m, n, p, q and r to vary independently between the different groups R2 and R3.

3. A composition comprising at least one compound of claim 1.

4. A composition according to claim 1, further comprising a nucleic acid.

5. A composition according to claim 4 in which said nucleic acid is a deoxyribonucleic acid.

6. A composition according to claim 4 in which said nucleic acid is a ribonucleic acid.

7. A composition according to claim 4 in which said nucleic acid comprises a therapeutic gene.

8. A method for introducing nucleic acid into a cell comprising contacting said cell with said nucleic acid and a compound according to claim 1.

9. A method according to claim 8 including incubating said cell with said nucleic acid and said compound.

10. A method for introducing nucleic acid to a patient comprising administering to said patient said nucleic acid and a compound according to claim 1.

11. A method according to claim 10 wherein said administration is effected by a topical route.

12. A method according to claim 10 wherein said administration is effected by a parenteral route.

13. A method according to claim 12 including injecting an organ.

14. A method according to claim 10 including introducing said nucleic acid into the nucleus of the cells of said patient.

* * * * *